United States Patent [19]

Moench et al.

[11] Patent Number: 5,592,949

[45] Date of Patent: Jan. 14, 1997

[54] DEVICE FOR ACIDIC BUFFERING AND METHOD FOR INACTIVATION OF PATHOGENS

[76] Inventors: Thomas R. Moench, 703 Stags Head Rd., Baltimore, Md. 21286-1446; Richard A. Cone, 225 W. Lafayette Ave., Baltimore, Md. 21217

[21] Appl. No.: 266,777

[22] Filed: Jun. 29, 1994

[51] Int. Cl.$^6$ ............................................. A61F 6/06
[52] U.S. Cl. ............................................. 128/837
[58] Field of Search ........................... 128/837, 834, 128/832, 830

[56] References Cited

U.S. PATENT DOCUMENTS

| | | |
|---|---|---|
| 2,141,040 | 12/1938 | Holt . |
| 2,616,426 | 11/1952 | Gordon . |
| 3,015,598 | 1/1962 | Jones . |
| 3,091,241 | 5/1963 | Kellett . |
| 3,128,767 | 4/1964 | Nolan . |
| 3,216,422 | 11/1965 | Steiger . |
| 3,983,874 | 10/1976 | Davis . |
| 4,274,410 | 6/1981 | Chvapil . |
| 4,360,013 | 11/1982 | Barrows . |
| 4,369,773 | 1/1983 | Chvapil . |
| 4,634,438 | 1/1987 | Sustmann et al. . |
| 4,634,439 | 1/1987 | Sustmann et al. . |
| 4,848,363 | 7/1989 | Cattanach . |
| 5,044,376 | 9/1991 | Shields ............................ 128/837 |
| 5,156,164 | 10/1992 | LeVeen et al. ................... 128/832 |
| 5,269,321 | 12/1993 | MacDonald et al. ............ 128/834 |

FOREIGN PATENT DOCUMENTS

| | | | |
|---|---|---|---|
| 2463609 | 8/1979 | France ........................... | 128/830 |

OTHER PUBLICATIONS

Holst et al., Treatment of Bacterial Vaginosis in Pregnancy with a Lactate Gel, Scand. J. Infect. Dis., 22:625–626, 1990.

Kempf et al., Virus Inactivation During Production of Intravenous Immunoglobulin, Transfusion, vol. 31, No. 5, pp. 423–427, 1991.

Leveen et al., Chemical Acidification of Wounds—An Adjuvant to Healing and the Unfavorable Action of Alkalinity and Ammonia, Annals of Surgery, vol. 178, No. 6, pp. 745–753, 1973.

Martin et al., Disinfection and Inactivation of the Human T Lymphotropic Virus Type III/Lymphadenopathy-Associated Virus, The Journal of Infectious Diseases, vol. 152, No. 2, pp. 400–403, 1985.

McCutchan et al., Role of Urinary Solutes In Natural Immunity to Gonorrhea, Infection and Immunity, vol. 15, No. 1, pp. 149–155, 1977.

Schlievert et al., Production of Staphylococcal Pyrogenic Exotoxin Type C: Influence of Physical and Chemical Factors, The Journal of Infectious Diseases, vol. 147, No. 2, pp. 236–242, 1983.

*Primary Examiner*—Jessica Harrison
*Assistant Examiner*—Michael O'Neill
*Attorney, Agent, or Firm*— Bell, Boyd & Lloyd

[57] ABSTRACT

The present invention is for a device and a gel method for controlling pH by acidic buffering. The device is made of a flexible dome, a flexible circular rim and an absorbent acidic buffer. The flexible dome is attached at its margin to the circular rim and the absorbent acidic buffer is contained within the device. The absorbent acidic buffer can control or maintain pH within physiological ranges. The gel method for controlling pH by acidic buffering is accomplished by applying a gel to an area where the pH is to be controlled. The gel includes an acidic buffering polymer which can control or maintain the pH of the area within the range of about 3 to about 5.

14 Claims, 1 Drawing Sheet

DEVICE FOR ACIDIC BUFFERING AND METHOD FOR INACTIVATION OF PATHOGENS

BACKGROUND OF THE INVENTION

1. Field of the Invention

The present invention relates to a device and method for maintaining or controlling pH by acidic buffering with an absorbent acidic material or an acidifying polymer gel.

2. Description of the Related Art for the Device

There is a need for improved methods for preventing sexually transmitted diseases (STDs) and unwanted pregnancy, for menstrual collection with a reduced risk of staphylococcal toxic shock syndrome, and for maintaining normal and protective vaginal flora that prevent vaginitis, vaginosis, and urinary tract infections. The present invention is based on the realization that a method providing rapid and reliable control of vaginal pH could provide a highly effective, yet highly physiologic means to achieve all these goals. This pH control is achieved by means of a vaginal diaphragm that provides prophylactic, contraceptive, hygienic, and therapeutic benefits by means of appropriate acidic buffers reliably and stably positioned over the uterine cervix.

The most effective contraceptive methods (sterilization, intrauterine devices, and contraceptive hormones) provide no protection against STDs. Barrier contraceptive methods such as condoms, diaphragms, and vaginal spermicides help prevent STD transmission by interposing a mechanical or chemical barrier between the female and the male, most importantly between the uterine cervix and the glans and urethral orifice of the penis. This barrier action is effective because secretions from these sites (cervical mucus and semen) are the most important sources of STD pathogens and also because these sites are the most susceptible targets for many STD pathogens. However, current barrier methods suffer from poor acceptance and therefore poor efficacy because they are inconvenient to use, and/or have undesirable toxicity. Male and female condoms are cumbersome to use and may reduce sexual pleasure and intimacy. Vaginal spermicides can erode the mucosa if used too frequently, and even with infrequent use, can disrupt the protective normal vaginal flora.

Presently available catamenial devices have limitations in convenience, comfort and safety. External absorbent pads are bulky, inconvenient, and associated with odor. Tampons are composed of fibers that may adhere to and abrade the mucosa during insertion or withdrawal, and that also may cause excessive drying due to direct contact of the absorbent fibers with the mucosa. Non-absorbent intravaginal catamenial devices may suddenly spill large amounts of menses fluid and are messy during removal. Tampons and other internally worn devices have been associated with overgrowth of toxin-producing *Staphylococcus aureus* possibly resulting in fatal staphylococcal toxic shock syndrome.

The pH of a healthy vagina is mildly acidic (pH 3.5–4.5) and this acidity is thought to be generated by the production of lactic acid by lactobacilli, which form a major component of the healthy vaginal flora. Together with other factors, this acid pH is widely recognized to prevent overgrowth of undesirable endogenous microbes (Candida, harmful anaerobes, and bacteria that may cause urinary tract infections) and encourages the continued dominance of lactobacilli which, in addition to mild acidity, provides other protective mechanisms such as production of hydrogen peroxide.

It is also known that sperm are inactivated by the mild acidity of the healthy vagina, and acid substances have been used as home made vaginal contraceptives for centuries. More recently it has been recognized that many sexually transmitted disease pathogens, *Neisseria gonorrhea* (McCutchan 1977), *Treponema pallidum, Haemophilus ducreyi*, and most or all enveloped STD viruses (Kempf 1991, Martin 1985) including herpes simplex virus, cytomegalovirus, and human immunodeficiency virus, are also inhibited or inactivated by mild acidic pH. However, semen contains a potent alkaline buffering capacity that neutralizes the vaginal acidity for a period of many hours after intercourse. This alkaline buffering capacity enables sperm to swim from the vagina into the cervix and upper genital tract.

Unfortunately, STD pathogens in genital secretions can also exploit this period of neutral vaginal pH, since it allows time for them to reach and infect their target cells. If this semen-induced neutralization of vaginal acidity could be promptly and reliably overcome, both contraception and STD prevention could be achieved by a method that closely mimics the normal physiological state of the vagina.

Maintaining an acid vaginal environment during menstruation would also have benefits. During menses, the protective vaginal acidity is temporarily lost due to the rate at which neutral and strongly buffering menstrual fluid enters the vagina. Consequently, acid inhibition of deleterious vaginal flora (such as *Staphylococcus aureus, Candida albicans*, harmful anaerobes, and bacteria that may cause urinary tract infections) is lost for a period of 4–7 days each menstrual cycle.

In addition, the elevated pH also allows certain strains of *Staphylococcus aureus* to produce toxic shock toxin I, whereas production of this toxin is completely inhibited at acidic pH$\leq$5.0 (Schlievert 1983). Thus, loss of protective acidity may result in staphylococcal toxic shock syndrome, candida vaginitis, bacterial vaginosis, or urinary tract infection.

Reestablishing vaginal acidity may be therapeutic in reversing established vaginitis (candida and trichomonas vaginitis) and the non-inflammatory condition termed bacterial vaginosis. (Bacterial vaginosis is characterized by an elevated vaginal pH due to reduction in lactobacilli populations and increase in other vaginal anaerobic bacteria.) The transition of *Candida albicans* yeast forms to the hyphal form (the form responsible for tissue invasion) is strongly inhibited at acid pH. The mucosal adherence of *Trichomonas vaginalis*, the cause of trichomonas vaginitis, is reduced at acid pH.

Acid pH is inhibitory to the harmful anaerobes whose overgrowth is associated with the malodorous discharge of bacterial vaginosis. Attempts have been made to treat these conditions with acidifying gels (for example, Lactal™, ACO, Stockholm, Sweden and Aci-jel™, Ortho Pharmaceutical Corp., Raritan, N.J.), with some success (e.g., Holst, 1990). The effectiveness of these products is limited, however, by their limited buffering capacity, and the fact that they may drip out of the vagina and the acidic agent may be absorbed across the vaginal mucosa. The clinical results indicate that a method that provided greater acidic buffer capacity, and that used a buffer that could be fully retained in the vagina would improve the therapeutic performance of this method for treating common vaginal infections.

Finally, it is known that during pregnancy, bacterial vaginosis may result in an increased incidence of pregnancy complications including urinary tract infections, premature delivery, and postpartum complications. As mentioned above, vaginal acidity is thought to be a factor inhibiting the overgrowth of these harmful anaerobes, and a method that safely maintains or restores vaginal acidity would have utility in preventing these pregnancy and postpartum complications. Such a method would avoid the risks of using drugs during pregnancy that may entail mutagenic or other toxic risks for the fetus.

Despite the recognition that acidic buffering of the vagina could protect against many STDs and other deleterious vaginal conditions, an appropriate vaginal buffering strategy has not previously been devised. Many buffers that might be employed would be ineffective due to their toxicity. The acidifying power required is large (approximately 0.5 milliequivalents of HCl to acidify a 5 ml ejaculate or 5 ml blood to below pH 5), and many types of acidic buffers would be excessively hypertonic and/or caustic if employed in sufficient dose. Second, many possible buffers are small molecules that rapidly leave the vagina by diffusing through the vaginal mucosa, thus limiting the duration of protection they can provide.

Third, the crucial importance of proper positioning of the buffering agent so that it forms a protective barrier between the uterine cervix and the penile urethra has not previously been recognized. The cervix is an anatomic site of great vulnerability not only because it is the portal for fertilizing sperm, but because the cervix is the primary target for many STD pathogens and, if infected, both the penile urethra and uterine cervix are primary sources of STD pathogens.

Fourth, the protective efficacy of an acidic buffer can be enhanced by factors that speed the ability of the buffers to acidify semen and menstrual fluid. Rapid acidification depends not only on adequate buffering capacity, but on configuring the buffering device to minimize the diffusion distance for the acidifying protons. This minimization can be achieved by preventing semen or menstrual fluid from pooling in cul-de-sac areas such as the vaginal fornix. In addition, diffusion time can be greatly reduced by making the device rapidly absorptive of body fluids, thus sequestering the bulk of semen or menstrual fluid away from contact with the mucosa and bringing these fluids into direct contact with the buffer.

U.S. Pat. No. 4,360,013 discloses a contraceptive device comprising a cylindrical, absorbent, acidifying sponge composed of alginic acid or other carboxylated polysaccharides, thus employing acidity to inactivate sperm. The possible utility of acid-buffering for STD prevention or menses collection were not recognized. Moreover, the device fails to provide an adequate physical barrier to prevent direct contact of semen with the cervical os since a sponge-like device that lacks a resilient rim to stabilize its position may be driven up into the vaginal fornix (FIG. 2) during sexual intercourse. Finally, the material specified for this device has a relatively low buffering capacity for its weight and bulk, and therefore to be effective the quantity of the sponge material required is excessively bulky, and likely to interfere with sexual intercourse.

U.S. Pat. No. 4,369,773 discloses a novel contraceptive vaginal diaphragm design which impregnates a sponge material with a detergent spermicide in an unspecified quantity of 0.1 molar citric acid buffer, pH 4.5. The use of this low molecular weight buffer is disadvantageous since it has the potential to be absorbed by and toxic to the mucosa. Moreover, the patent does not provide data or make claims on the potential contribution of the buffer to the spermicidal activity of the detergent, nor does it discuss or recognize the potential of acid-buffering as an STD deterrent, nor does it specify the buffer capacity needed to achieve STD deterrent or contraceptive effect. The device suffers from the disadvantages of detergent spermicides which may irritate the mucosal tissues and disturb the normal vaginal flora.

Several other known contraceptive methods employ intravaginal sponge-like materials with semen absorbing capability, U.S. Pat. No. 4,393,871 (the Today Sponge™) and U.S. Pat. No. 4,274,410. However, the former patent relies predominantly on a detergent spermicide for contraceptive efficacy, thus suffering from the potential toxicity of detergents. The latter patent alludes to the possibility that its formulation at acid pH may be beneficial in aiding the normal vaginal acidity in inhibiting harmful microbes and inactivating sperm. However, the patent fails to determine the buffering capacity required to achieve such advantageous effects, and fails to determine or specify the buffering capacity of the device. Moreover, neither of these devices have an elastic rim and hence may be driven up into the vaginal fornix during sexual intercourse where they will fail to provide a reliable physical barrier that prevents direct contact of the cervical os and penile urethra.

The prior art discloses patents describing catamenial devices composed of carboxylated cellulose fiber (U.S. Pat. Nos. 4,634,438 and 4,634,439) providing for maintenance of vaginal acidity during collection of menstrual fluid. U.S. Pat. No. 3,091,241 discloses a tampon impregnated with triacetin intended to release acetic acid to maintain an acid vaginal pH during menses. However, this device introduces a new metabolizable substrate which may alter vaginal flora in unknown ways, and this method would be so slow in acidifying semen that it would provide little or no protection.

Both of these inventions suffer from the disadvantages of conventional tampons, namely the potential for excessive drying of the mucosa due to direct contact of the absorbent fibers, and for abrasive trauma inherent in exposed fibrous absorbents. The potential for STD deterrence provided by acid is not recognized in these patents. Moreover, all these methods would be poorly suited to use during sexual intercourse because they obstruct the vaginal lumen and provide no reliable barrier to protect the cervix.

There are several known catamenial devices designed to be worn in the upper vagina covering the cervical os and thus collecting menstrual blood as it exits the os (U.S. Pat. Nos. 2,141,040; 2,616,426; and 4,848,363). These methods suffer from potential spillage of fluid during wear or upon removal (since they are non-absorptive), and are incapable of maintaining normal acid vaginal pH to protect against toxic shock. Absorptive upper-vaginal catamenial devices have been disclosed (U.S. Pat. Nos. 3,128,767; 3,983,874; and 3,216,422) but are incapable of maintaining normal acid vaginal pH.

Conventional contraceptive diaphragms known in the prior art do provide an effective stably positioned mechanical barrier for the cervix, but they also rely on detergents or other spermicides to enhance contraceptive and disease preventive efficacy. These diaphragms thus increase the risk of toxicity toward the mucosa and the disruption of normal vaginal flora because of the properties inherent in these spermicides.

U.S. Pat. No. 3,015,598 discloses a fibrous, absorptive, spermicidal, contraceptive diaphragm, where in one embodiment the sperm cells are absorbed into a spermicidal absorbent layer. This patent does not disclose a device or a method for acidifying an ejaculate or for acidifying menstrual fluid.

We have invented a device enabling control of vaginal pH for the prevention of sexually transmitted disease and unwanted pregnancy, for the maintenance or restoration of healthy vaginal flora, and for collection of menstrual discharge while maintaining a healthy vaginal pH.

The device positions advantageous quantities of appropriate buffers in a dome shaped configuration that provides stable positioning of the device around the cervix. The large surface area of the device and its resilient circular shape cause it to project into the posterior vaginal fornix, gently spreading the vaginal mucosa against the surface of the device, thus preventing pooling of the ejaculate in a relatively inaccessible cul-de-sac. The device is highly absorptive, and rapidly sequesters and acidifies both semen and menstrual fluid.

The present invention avoids the toxicity of conventional spermicides by providing sufficient acidic-buffering capacity to overcome the neutralizing capacity of the ejaculate and thereby achieves contraception and disease prevention by maintaining the normal protective acid vaginal pH.

SUMMARY OF THE DEVICE

The present invention is for a device or apparatus for controlling pH by acidic buffering. The device is comprised of a flexible dome, a flexible circular rim and an absorbent acidic buffer. The flexible dome is continuously attached at its margin to the circular rim and the absorbent acidic buffer is contained within the device or apparatus. The acidic buffer may be contained on the concave surface, on the convex surface, or on both surfaces of the dome and can maintain or control pH within physiological ranges.

DETAILED DESCRIPTION OF THE PRESENTLY PREFERRED EXEMPLARY EMBODIMENTS FOR THE DEVICE

Figure 1:
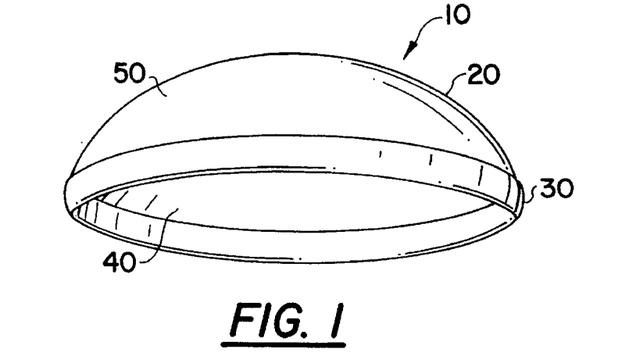
FIG. 1 is a perspective view of a device for controlling or maintaining pH within physiological ranges by acidic buffering.
Figure 2:
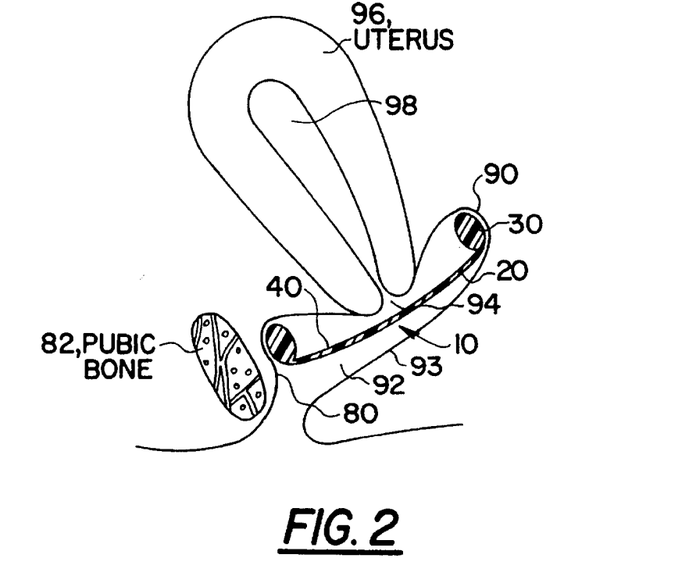
FIG. 2 is a cross-sectional view of a device in place in upper vagina, (92) residing anteriorly on the "ledge" (80) formed by the pubic bone (82) and extending posteriorly well into the vaginal fornix (90). The vaginal lumen (92), vaginal wall (93), uterus (96) and uterine cavity (98) are also shown in this cross-sectional view.

The essential features of the invention are these:

1) A disposable device (10) with a configuration like that of a conventional contraceptive diaphragm (FIG. 1), i.e., a thin and flexible dome (20) attached at its margin to a flexible circular rim (30) designed for wear in the upper vagina with the rim (30) encircling the uterine cervix, (94) the cervix projecting into the concavity of the dome (FIG. 2). The device thus provides a reliable and complete mechanical barrier between the cervix and the penile urethra without obstructing the vaginal lumen during sexual intercourse. This configuration prevents direct contact and exchange of pathogens and sperm between the penis and the cervix, yet avoids obstruction of the vaginal lumen. The rim (30) has sufficient resilience to retain it in place, residing anteriorly on the internal "ledge" created by the pubic bone (82) and projecting posteriorly well into the vaginal fornix (90). In this position, the circular resilient rim (30) gently spreads the vaginal mucosa in close approximation to the large area of the dome (20), thus preventing pooling of the ejaculate in an inaccessible cul-de-sac. The circular rim (30) has a diameter of 5–10 cm, preferably about 7 cm.

2) The dome (20) is made with a material impervious to the passage of sperm, STD pathogens in semen or in cervical mucus, and white blood cells in these secretions that may carry pathogens. For example, the dome (20) can include a layer of flexible film such as silicone, polyethylene, polyurethane, or other impervious flexible film. Not only will this impervious dome (20) function to prevent pathogens and semen from the male from direct and immediate contact with the cervix, but it likewise functions to prevent pathogens from the female (many of which are found predominantly in the cervical secretions) from direct and immediate contact with the penis of the male. Moreover, this physical barrier covering the cervix also greatly enhances the ability of the mildly acidic buffer to act on STD pathogens and sperm because they must be well-exposed to the buffer before they can reach susceptible tissues of the other sexual partner, regardless of which partner is infected.

3) The dome (20) contains an adequate supply of buffer to acidify at least one large ejaculate of human semen, cervical secretions for at least 8 hours, or at least 10 ml of menstrual fluid to a pH below 5.5, preferably below 5.0, as a result of its buffering action.

4) The dome (20) contains absorptive material that can rapidly absorb semen and/or menstrual fluid. Advantageously, the buffer is chosen to be an intrinsically absorptive material, an absorptive buffer. This absorptive buffer provides multiple benefits, including: a) reduction of the time required to acidify body fluids (by reducing diffusion distance), b) sequestration of pathogens by drawing the bulk of the body fluids away from contact with the mucosa, c) reducing "post-coital drip", that is, the discharge of semen and vaginal fluids after intercourse, and d) providing a convenient and mess-free method to collect menstrual discharge.

The absorptive buffer can be composed of a high molecular weight polymer made from monomers containing a buffer group with a pKa of between 4 and 6, and used either in its unadjusted acidic form, or if necessary, adjusted to a pH of approximately 3–4. The polymer thus releases protons as needed to maintain the healthy and protective vaginal pH of about 4, and effectively resists a rise in pH caused by a preexisting elevated vaginal pH (as is often the case in vaginal infections or in postmenopausal women), or by the arrival of neutral or alkaline menses and semen. A non-limiting example of such an advantageous polymer is a crosslinked carboxylated polymer, most preferably, crosslinked polyacrylic acid or polymethacrylic acid. Such crosslinked polymers are commonly used for diapers and feminine hygiene products. However, as currently practiced, these products use neutralized polyacrylic acid (60 to 80% neutralized to a pH of 5.5–7.0), since the absorbent capacity of the materials is maximal at neutral pH and since the benefits of using the polymers as absorptive acidic buffers to maintain vaginal acidity were not previously recognized.

To maintain vaginal acidity during menses it is necessary to limit the absorbent capacity of the device (10) to that amount of menstrual fluid that it can adequately acidify. Thus, for the present application it may in fact be advantageous to reduce the superabsorbency of the buffer even more than the reduction caused by using the absorbent buffers in their acidic form. This reduction can be achieved by increasing the crosslink density of the crosslinked polyacrylic acid by any of several methods well known in the art. Additional crosslinks reduce the absorbing capacity while only slightly altering the acidifying buffer capacity of the material. Other ways of reducing absorbency without reducing acidifying buffer capacity include addition of divalent cations such as calcium or magnesium, or physically constraining the swelling of the absorbent buffering material, for example, by entrapping particles of the absorbent in a thermally bonded meshwork of polypropylene or polyester fibers. Any of these methods can be used to ensure that all fluid absorbed by the device will be adequately acidified, and that the user will remove the device when the menstrual flow has exceeded its absorptive capacity but not its buffering capacity.

EXAMPLE 1

Twenty grams of a crosslinked polyacrylate superabsorbent powder (Aridall 1460™, Chemdall Corp., Palatine, Ill.) were soaked for 16 hours in 400 ml of 0.25M HCl. The acidified powder was subsequently washed extensively with methanol over a Buchner funnel and then dried under vacuum. When 200 mg of the acidified powder was suspended in 18 ml of saline, the pH was 3.8. The buffering capacity of this material is high: 1.4 milli-equivalents of sodium hydroxide are required to raise the pH of this suspension from 3.8 to 7.0, thus 7 milli-equivalents per gram of powder.

EXAMPLE 2

Aliquots of this acidified superabsorbent were used to acidify one ml of human semen by sequential addition of the superabsorbent, mixing to homogeneity, then recording the pH after a 10 minute equilibration period after each addition. The results are shown in Table 1.

TABLE 1

| Acidification of 1 ml of semen by acidified superabsorbent. | | |
|---|---|---|
| Superabsorbent added | Cumulative superabsorbent added | pH of semen |
| 0 mg | 0 mg | 7.57 |
| 10 mg | 10 mg | 5.78 |
| 10 mg | 20 mg | 5.29 |
| 10 mg | 30 mg | 5.00 |
| 20 mg | 50 mg | 4.64 |

The significance of the ability of the acidified-superabsorbent to acidify semen is two-fold. First, as mentioned above it is known that many STD pathogens from the male are predominantly contained in the semen, and it is further known that they can be inhibited and/or killed by an acid pH. Second, it is known that sperm are immobilized at acid pH.

EXAMPLE 3

To test the ability of the acidified superabsorbent to immobilize sperm by acidification, 0.5 ml of human semen (initial sperm motility>90%) was mixed with 10 mg of the acidified superabsorbent. At intervals after mixing, a portion of the mixture was removed, diluted 3:1 with saline (to reveal sperm motility), and sperm motility assessed by microscopy. At 5 min only about 5% were motile, and at 10 min motility was abolished.

In contrast, when the original superabsorbent powder (without acidification) was substituted for the acidified powder in an otherwise identical experiment, no significant change in sperm motility was observed after 10 min incubation.

It would thus require approximately 0.1 gram of this material on the convex side (50) of the dome (20) to inactivate 5 ml of semen. Since the ejaculate is not likely to be evenly distributed over the dome (20), it is advantageous to employ as large a buffering capacity as is practical to fully acidify semen collected in localized regions, as well as larger ejaculates, or multiple ejaculates.

The practical upper limit is set by the volume or bulk of the device and by the intrinsic capacity of the buffer (milliequivalents/gm). The device (10) would become excessively bulky for the vagina if more than about 10 grams of acidifying absorbent buffer was used on the convex surface (50) of the dome (20). Thus, between 0.1 and 10 grams of acidifying superabsorbent should be incorporated into the outer surface (50) of the dome (20), preferably about 1 gram.

As an alternative to measuring buffer capacity of various possible buffering polymers with respect to semen acidification, buffer capacity is more conveniently measured with respect to its ability to maintain a protective pH (pH≦5) in the face of the addition of sodium hydroxide.

EXAMPLE 4

100 mg of acidified superabsorbent polymer prepared in Example 1 was suspended in physiological saline. This suspension was titrated with sodium hydroxide and monitored with a glass combination electrode. 14 mg (0.35 meq) of sodium hydroxide was required to raise the pH of the suspension from its initial pH of 3.8 to a pH of 5.0. Thus, the buffering capacity of devices containing from about 0.1 to about 10 grams of the superabsorbent material described in Example 1 would be adequate to maintain a pH≦5 (measured in physiological saline) after addition of between 0.014 g and 1.4 g of sodium hydroxide.

EXAMPLE 5

The ability of the acidified superabsorbent to acidify blood was tested in an experiment identical to that performed in Table 1 above except that fresh, heparinized, venous, human blood was substituted for semen. The results are shown in Table 2.

TABLE 2

| Acidification of 1 ml of blood by acidified superabsorbent. | | |
|---|---|---|
| Superabsorbent added | Cumulative superabsorbent added | pH of blood |
| 0 | 0 | 7.80 |
| 10 mg | 10 mg | 6.58 |
| 10 mg | 20 mg | 5.52 |
| 10 mg | 30 mg | 5.09 |
| 20 mg | 50 mg | 4.69 |

At pH≦6.0, TSST-1, the toxin responsible for staphylococcal toxic shock syndrome, is not produced. Thus, the acidified superabsorbent has the capacity to acidify an advantageous amount of menstrual fluid, thus maintaining a beneficial acid vaginal pH, and preventing staphylococcal toxic shock syndrome associated with menstruation.

EXAMPLE 6

To determine whether the absorbent capacity of the acidified-superabsorbent is still adequate to function effectively as a superabsorbent and to compare it to the original unaltered superabsorbent, 0.5 grams of acidified, or unaltered, superabsorbent were added to 50 ml of saline, and shaken for 10 min to allow swelling to equilibrium. The swelled absorbent was compressed in a water permeable non-absorbent fabric bag at a pressure of 0.3 pounds per square inch for 2 minutes. The swelled absorbent was weighed, and the amount of saline retained calculated. The acidified material retained 18.3 grams of saline per gram of absorbent, and the original (non-acidified) absorbent retained 30.6 grams per gram. Thus, acidification resulted in a 40% reduction in the absorbent power of the superabsorbent, but the residual absorbent power is still more than adequate for the purpose of the present invention since one gram of acidified absorbent will retain at least 18 ml of menses fluid, an amount greater than that absorbed by "superabsorbent" tampons. Moreover, 18 ml of blood absorbed by one gram of acidified superabsorbent would be acidified to a pH below 4.7 according to the observations made in Table 1, thus reducing the risk of menstrual related staphylococcal toxic shock syndrome.

It is desirable to provide enough acidifying superabsorbent on the inner (concave) surface (40) of the dome (20) to allow the device (10) to absorb and acidify at least 10 ml of menstrual fluid, that is, approximately 0.5 grams. However, the device (10) would probably become excessively bulky if more than 10 grams of acidifying superabsorbent was used on the concave surface (40) of the dome (20). Thus, between 0.5 and 10 grams of acidifying superabsorbent should be incorporated into the concave surface (40) of the dome (20), preferably about 1 gram.

It is emphasized that there are many other acidifying superabsorbent materials that could be used for this purpose, as there are many commercially available crosslinked polyacrylate superabsorbents. Furthermore, such materials could be manufactured with less than the usual 60–80% neutralization as practiced in the superabsorbent industry without undue technical difficulty, thus obviating the need for acid washing as used in the present example. Finally, it is emphasized that buffering materials other than crosslinked polyacrylic acids could also be used to achieve vaginal buffering via an upper vaginal diaphragm device. These include other carboxylated polymers, and polymers containing other proton donating chemical species.

Figure 3:
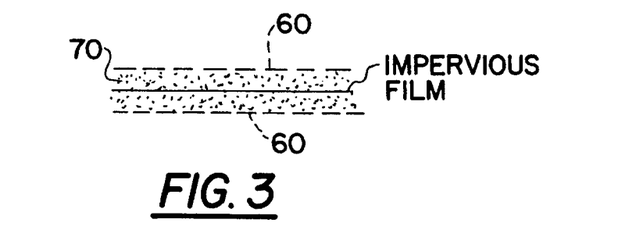
FIG. 3 is a magnified cross-sectional view of the dome laminate in an embodiment of a device for controlling or maintaining pH within the range of about 3.5 to about 5.0 by acidic buffering.

5.) Another embodiment of the invention consists of a device (10) constructed so that the surface of the dome (20) is covered by a non-adhesive and non-absorptive or minimally absorptive non-woven fabric coverstock (60) such as used on adhesive bandages, diapers, and menstrual pads (FIG. 3). The coverstock (60) would allow transfer of body fluids into the interior of the dome's absorptive material (via fenestrations) but does not allow direct contact, or adhesion, between the absorptive material and the mucosa. This selective transfer ability not only eliminates undesirable adhesion of the device (10) to the mucosal surface, (a problem with tampons) it also has the benefit of avoiding excessive drying of the mucosa which may occur with tampons. An example of an appropriate coverstock (60) material is Delnet™ CKX-215 (Applied Extrusion Technologies, Inc., Middletown, Del.). The advantages of using such non-adhesive coverstocks has not previously been recognized for use in upper vaginal diaphragms or catamenial devices.

EXAMPLE 7

To test the ability of acidified superabsorbent (70) covered by such a coverstock (60) to rapidly absorb, acidify, and retain semen, 1 gram of acidified superabsorbent powder (pH 3.7 tested in saline) was placed between two sheets of Delnet™ CKX-215, texturized, (Applied Extrusion Technologies, Inc., Middletown, Del.), with the powder spread over an area of 20 $cm^2$. One ml of freshly ejaculated, liquified, human semen containing the pH indicator dye bromocresol purple at a concentration of 0.002% was pipetted onto the surface of the coverstock (60). By 2 min the semen had soaked through the coverstock and had spread to an area of 7 $cm^2$ By 5 minutes the color of the indicator dye had changed from magenta to yellow, indicating that the pH had dropped to $\leq 5.2$. The semen was well retained in the acidified superabsorbent and did not drip out, nor could it be squeezed out with gentle pressure. Thus, the semen is promptly absorbed, acidified to a level that will immobilize sperm, and is adequately sequestered inside the coverstock (60) by the acidified-superabsorbent (70). The stirring action of coitus will further increase the speed with which semen is sequestered and acidified by this method.

6) The device (10) may also be constructed to provide buffering and absorbency on either or both sides of the pathogen-impervious barrier within the dome (20), and the buffering capacity and absorbency can be independently adjusted on each side of the dome (20) to achieve the most desirable product for a given application. In particular if both sides of the impervious barrier have the same composition and construction, then even if the device (10) is inserted "upside down", the side facing the cervix will still function to absorb and acidify menstrual fluid, and the side facing the vaginal lumen will still function to absorb and acidify semen. Moreover, with this symmetrical design, even after heavy menstrual flow, the side facing the vaginal lumen will be fully capable of absorbing and acidifying a large ejaculate. Alternatively, during heavy menstrual flow, if the user had no replacement available, the user could invert the cup to collect additional menses.

7) Another use for this invention is as a therapeutic device to aid healing of vaginal epithelial defects caused by surgery, trauma, infection, cancer, or other diseases. The acid environment created and maintained by the device would inhibit many harmful bacteria which might interfere with wound healing. Moreover, an acid environment is known to aid in the oxygenation of the tissues by shifting the hemoglobin dissociation curve to allow more complete unloading of oxygen to the tissue, thus speeding the healing process (Leveen 1973). To achieve this effect in the vagina, it is advantageous to employ a device (10) with high buffering capacity to maintain vaginal acidity in the face of entry of neutralizing fluids such as menses fluid and/or wound exudate, and to cover this device (10) with a non-adhesive coverstock (60) such as commonly used in adhesive bandages.

8) Another embodiment of the invention is as a device (10) wherein certain portions are reusable. For example, the rim (30) and a fenestrated coverstock (60) could be made to be reusable, and a disposable disk of absorbent buffering material inserted between two layers of coverstock. Thus, only the absorbent buffering disk need be discarded and replaced after it has absorbed and acidified semen or menstrual fluid. A second example would involve reusing the rim (30) only, and making the absorbent (70) and coverstock (60) both disposable. Making all or part of the device (10) reusable would minimize the environmental impact of disposable feminine hygiene products.

9) The device (10) can also be used to deliver and provide sustained release of one or more beneficial agents. The agents could be added to the absorbent buffer material of either surface of the dome (20), and would be released slowly by diffusion. Positively charged agents would be released even more slowly by an ion-exchange mechanism from the polyanionic matrix of the superabsorbent. Such agents could include spermicides, bactericides, viricides, fungicides, hormones, nucleic acids, proteins, vaccinogens, antibodies or cytokines, peptides, metal chelators, additional lower molecular weight acidic buffers or any other beneficial agents. The purposes of such agents could include contraception, prophylaxis, local or systemic treatment, vaccination, booster vaccination or other purposes.

While the device for acidic buffering has been described in connection with what is presently considered to be the most practical and preferred embodiments, it is to be understood that the device invention is not to be limited to the disclosed embodiments, but on the contrary is intended to cover various modifications and equivalent arrangements included within the spirit and scope of the appended claims.

DESCRIPTION OF THE RELATED ART FOR THE ACIDIFYING POLYMER GEL METHOD

Many types of sexually transmitted disease (STD) pathogens and sperm are readily inactivated at mildly acid pH and we disclosed above an acidic buffering device for hygiene and protection against STDs and pregnancy. We disclose here methods for controlling or maintaining pH by applying acidic buffering polymers as free gels directly to biological orifices, including the nose, mouth, ears, rectum,and vagina, and to skin. Such gels can act as protective sexual lubricants. People infected with STDs shed pathogens in semen, cervical, vaginal, rectal or oral secretions, or exudates from sores, blisters or chancres, on or near genital skin or mucosal surfaces and thereby transfer these pathogens to the sexual partner's skin and mucosa. Thus, a gel applied to these surfaces is ideally positioned to form a diffusional barrier that can also inactivate STD pathogens and thereby block their ability to transmit a disease.

Many buffers that might be used to prevent STD transmission or pregnancy would be ineffective due to toxicity. The acidifying power required is large: approximately 0.5 milliequivalent of HCl is needed to bring a typical 5 ml ejaculate to pH 5. Thus, a substantial quantity of buffer is needed, and many types of acidic buffers would therefore be excessively hypertonic and/or caustic if employed in a dose sufficient to be protective. Moreover, many possible buffers are small molecules that rapidly diffuse through mucosal surfaces, thus limiting the duration of protection they can provide at the susceptible surface, and causing toxic effects as they accumulate within mucosal cells.

Acidifying vaginal gels used to restore an acid vaginal pH and encourage growth of a normal lactobacillus dominated vaginal flora are known (Aci-jel™, Ortho Pharmaceutical Corp Raritan, N.J., and Lactal, ACO, Stockholm, Sweden). These products rely on acetic acid and lactic acid for their acidifying power, thus suffering from the disadvantages inherent in the use of small freely diffusible weak acid buffers, namely inadequate buffering capacity for the purpose of acidifying semen, loss from the mucosal surface via transmucosal diffusion, and the potential for mucosal toxicity.

Several products are known that make use of the bioadhesive and drug delivery properties provided by crosslinked polyacrylic acids such as Carbopol, and polycarbophil (Metrogel-vaginal, Curatek Phamaceuticals, Elk Grove Village, Ill.; Replens and Feminesse, Columbia Laboratories, Inc., Hollywood, Fla.). Some of these products are formulated for vaginal use at acid pH in order to mimic the normal vaginal pH. However, a method for using these polymers to acidify an ejaculate sufficiently to serve as a prophylactic against STD's or pregnancy was not known, and the products contain insufficient quantities of the acidifying polymers to be effective for this purpose.

SUMMARY OF THE METHOD

The present invention is for a method for controlling pH by acidic buffering. The acidic buffering is accomplished by applying a gel to an area where the pH is to be controlled. The gel is comprised of an acidic buffering polymer or polymers which can control or maintain the pH of the area between about pH 3 and about pH 5, and applied in a quantity sufficient to keep the area within this acidic pH range even after an ejaculate has been deposited. The gel may be applied to skin or to biological orifices, including mouth, ears, nose, rectum or vagina.

DETAILED DESCRIPTION OF THE PRESENTLY PREFERRED EXEMPLARY EMBODIMENTS FOR THE METHOD

The essence of the invention disclosed in this section of the patent is a method for controlling pH by acidic buffering. Such a method will result in the prevention of sexually transmitted diseases and pregnancy because of the application to the mucosa and skin of a buffering polymer of sufficient molecular size to render it poorly absorbable and of low osmotic activity, and of sufficient dose to achieve the acidification of at least 10 ml of human semen to a pH below 5.

We have discovered that highly carboxylated polymers, for example polyacrylic acids, overcome these problems and are highly satisfactory for the purpose of acidifying semen and maintaining mucosal surfaces at a protective acid pH. These polymers have a pKa of approximately 6.0, advantageously midway between the initial pH of semen (7.6–8.0) and many other secretions exchanged during sex, and the pH (4.0–5.0) needed to inactivate sperm and pathogens. These polymeric buffers are not hypertonic even at a strongly buffering dose since there are many buffering groups per osmotically active particle. Moreover, the buffering capacity is high for a given weight of polymer since the equivalence weight is low (i.e., there is approximately one mole of titratable groups per 75±5 grams of polyacrylic acid).

The polymers are very large (molecular weight 400,000 to $\geq 3,000,000$), and therefore do not diffuse into or through mucosal surfaces, which increases their duration of action and avoids systemic exposure and potential toxicity. Finally, some of these polymers produce highly entangled mucoadhesive gels that mimic and augment the protective function of mucus on mucosal surfaces by providing lubrication and forming an unstirred layer next to the mucosal surface that slows or prevents contact of pathogens with the mucosa.

Published data employing such polymers for wound acidification (using acidity to promote unloading of oxygen in the wound) demonstrates that both linear and crosslinked polyacrylic acids provide prolonged maintenance of acidic pH when applied to tissues and open wounds, and do so without apparent toxicity (Leveen '73). These polymers are poor substrates for bacterial growth, and are thus unlikely to disrupt normal microbial flora.

Although the present invention relies on the use of these materials in their predominantly free acid form, it is advantageous to partially neutralize the polymers (for example, approximately 20% neutralized with sodium hydroxide or potassium hydroxide to pH about 3 to about 4). Moreover, when partially neutralized in this manner aqueous dispersions of some of these materials (Carbopol® 934, 940, 941, 971, 974, 980, 981, 2984, 5984 and Noveon AA-1, BF Goodrich; Junlon PW110 and Junlon PW111, Nippon Junyaku, Osaka, Japan) make gels with excellent lubricity, high yield strength (resistance to dripping), mucoadhesiveness, nearly no odor or taste, and no deleterious effects on latex condoms. An aqueous gel containing highly carboxylated polymers thus has utility as a sexual lubricant capable of preventing the exchange or transmission of acid-sensitive STD pathogens and sperm during sexual activity.

When formulated as lubricants, such polymer buffers applied to external genitalia as well as internal mucosal surfaces not only will reduce microtrauma resulting from inadequate lubrication, but will also, by means of acid-induced inactivation, prevent transmission of viable STD pathogens through traumatized, diseased, or healthy skin or mucosa. To achieve maximum protection against multiple or large ejaculates, and to ensure that regardless of how the gel and the ejaculate(s) are distributed, it is advantageous to employ the maximum practical buffering capacity. The practical limit is set by the volume of gel that can be delivered and retained by the site to be protected, and by the maximum achievable buffer capacity of the gel with acceptable viscoelasticity.

EXAMPLE 8

Approximately 0.03 g of a polyacrylic acid polymer (Carbopol® 934P) mixed with water and partially neutralized (to pH 4) to form an aqueous gel, will acidify one ml of semen to pH≦0.5, as demonstrated in Table 3.

TABLE 3

| | Acidification of 1 ml of semen by 2% aqueous Carbopol ® 934P, pH 4. | | |
|---|---|---|---|
| Gel added (g) | Cumulative gel added (g) | Cumulative polymer added (g) | pH of semen |
| 0 | 0 | 0 | 7.82 |
| .3 | .3 | .006 | 6.49 |
| .3 | .6 | .012 | 5.69 |
| .3 | .9 | .018 | 5.30 |
| .3 | 1.2 | .024 | 5.10 |
| .6 | 1.8 | .036 | 4.79 |
| .6 | 2.4 | .048 | 4.60 |

Since the average ejaculate volume is 3.4 ml and since the results in Table 3 imply that 0.028 g polymer is required to acidify 1 ml semen to pH 5, at least 0.1 g polymer is needed to acidify an average ejaculate to pH 5, a pH which will inactivate sperm and STD pathogens.

Since ejaculate volumes often exceed 3.4 ml and since incomplete mixing of ejaculate and polymer is inevitable, more than 0.3 g of Carbopol® 934 partially neutralized to pH 4 (or an amount of an alternative polymeric buffer with an equivalent buffering capacity) is advantageous to achieve more reliable protection against both STD pathogens delivered in an ejaculate and pregnancy.

Indeed, within practical limits of vaginal volume and acceptable physical characteristics of the gel, the higher the buffer capacity, the more reliable will be the protection.

As an alternative to measuring buffer capacity with respect to semen acidification, buffer capacity is more conveniently measured with respect to its ability to maintain a protective pH (pH≦5) after addition of sodium hydroxide.

EXAMPLE 9

Ten ml of a 1% aqueous dispersion of Carbopol 934P (thus, 100 mg of polymer) in physiological saline, was titrated with sodium hydroxide while monitoring the pH with a glass combination electrode.

15 mg (0.37 meq) of sodium hydroxide was required to raise the pH of the gel from pH 4.0 to pH 5.0. Thus, the effective buffering capacity of 0.1 g polymer at pH 4 is just sufficient to maintain pH≦5 after adding 15 mg of NaOH.

Therefore, the buffering capacity required per dose for the practice of this method is that capacity capable of maintaining a pH≦5 (measured at physiologic salt concentration) after addition of a minimum of 15 mg sodium hydroxide.

A further advantage of constituting the buffer as a gel-forming polymer is that in this form, the buffer mimics and augments the protective effect of mucus that naturally covers mucosal surfaces. Like mucus, the polymer provides protective lubrication, and provides an unstirred layer which increases the distance through which pathogens must diffuse or move by active motility. This increases the time available for acid-inactivation of pathogens before they can contact target tissues. The bioadhesive nature of these acidifying polymers further enhances their ability to act as barriers to protect the mucosa.

An additional advantage of constituting the buffer as a gel-forming polymer is that in this form the acidic buffer is highly toxic for particles (sperm, infected white blood cells, and free pathogens) that are immersed within the gel, but is much less toxic to mucosal cells.

Since the polymer buffer forms an unstirred layer over the mucosa, the proton concentration at the mucosal surface becomes depleted since the mucosa with its supporting blood supply can act as an effective proton sink. Thus, the intracellular pH of the mucosal cells can be maintained at near normal levels since the rate at which additional protons arrive at their surface is limited by diffusion through the unstirred layer of gel.

In contrast, a cell or pathogen suspended in the interior of the gel cannot defend or maintain its pH by exporting protons to an adjacent blood supply or mass of tissue, and hence individual cells and pathogens surrounded by the gel are rapidly inactivated.

EXAMPLE 10

We have discovered that the rectum can easily hold 60–120 ml of a 2% Carbopol® 934P (BF Goodrich, Cleveland, Ohio) aqueous gel (see example formula below), applied via an enema applicator (Comfortip®, Fleet Pharmaceuticals, Lynchburg, Va.).

We have further discovered that this large volume of gel is easily retained in the rectum without discomfort, does not drip out, and does not cause an urge to defecate. It provides a volume sufficient to achieve total coverage of the large rectal surface area (150–200 $cm^2$), and maintains a pH<4.5 in the rectum for more than 1 hour.

Thus, it is possible to apply an adequate dose to the interior of the rectum that will result in the distribution over an extensive area of a quantity of buffer gel adequate to cause rapid and complete acidification of an ejaculate deposited during rectal intercourse.

The acidifying buffer can be used for rectal, vaginal or oral intercourse, and can also be used with a condom, to protect against skin-to-skin or sore-to-sore transmission of pathogens, and to give additional protection in the event the condom slips, breaks or leaks.

EXAMPLE 11

A non-limiting example of preparation of such a gel is as follows:

| | |
|---|---|
| Distilled water | 93.5 ml |
| KCl | 0.15 g |
| EDTA, 0.5M | 0.1 ml |
| Carbopol ® 934P NF (BF Goodrich) | 2.0 g |
| NaOH, 10N | 0.4 ml (final pH approx. 4) |
| Mannitol | 3.83 g |

The above ingredients are added and mixed in the order given in an electric mixer, sprinkling the polyacrylic acid polymer slowly over the rapidly mixing surface of the aqueous solution. The result is an opalescent, moderately viscous gel. Additional or alternative salts, viscosity and lubricity modifiers, metal chelators (e.g., lactoferrin or EDTA), antioxidants, flavorings, preservatives, monomeric or oligomeric buffers (e.g., lactic, acetic or citric acid), spermicidal detergents, polysulfonated polymers, vaccinogens, antibodies, or other beneficial agents can be added.

It is advantageous that the lubricant be nearly isotonic for application in contact with the mucosa. Mucosal surfaces are highly permeable to water and can thus rapidly change the volume and viscosity of the lubricant, decreasing the volume of the gel and increasing its viscosity if it is hypotonic, or expanding its volume and reducing its viscosity if the gel is hypertonic. Marked departure from isotonicity may also be toxic to some mucosal epithelia. Mannitol is chosen as an example of an advantageous osmolyte to adjust the tonicity of the lubricant since mannitol is of low molecular weight, non-toxic, very poorly absorbed, and only minimally metabolizable by bacteria.

Greater buffering power can be added to the gel to reduce the volume of gel needed to acidify an ejaculate. This increase in buffering power will reduce the volume of gel needed to be delivered to the surface in need of protection. To increase buffering power, the concentration of gel-forming crosslinked polyacrylic acid polymers such as Carbopol® 934 can be increased to about 3% before excessive viscosity becomes limiting. If additional salts such as NaCl, KCl, $MgCl_2$, or $CaCl_2$ are added, they reduce viscosity which allows the polymers to be used in concentrations up to 6%.

For even greater buffering power, linear (non-crosslinked) buffering polymers (e.g., linear polyacrylic acid, MW 200,000–2,000,000, Polysciences, Inc., Warrington, Pa.) can be added at concentrations between about 1 and 5% with an acceptable increase in viscosity. Alternatively, a crosslinked but relatively inefficient gel-forming polymer such as Carbopol® 910 can be employed, thereby advantageously allowing a high polymer concentration and yet a low viscosity. A limitation of these last two approaches is that they become "sticky" when used at high polymer concentrations.

Alternatively, novel forms of crosslinked polyacrylic acid polymers can be created with properties optimized specifically for the present purpose, that is maximizing buffer capacity while avoiding excessive viscosity or stickiness. This optimization can be achieved by synthesis of a polymer with a sufficiently high crosslinking density to make it only minimally swellable and minimize entangling of extended polymer chains. This synthesis results in "ball-bearing-like" structures that contain a concentrated mass of buffer, but easily slide over one another with low viscosity and stickiness. This structure and characteristics can be achieved simply by increasing the quantity of crosslinker monomer, (for example, polyallyl-sucrose) above the commonly used fraction of 0.01 to 2% of the mass of acrylic acid monomer. The reduction of polymer swellability by increasing crosslinking is well known. Highly carboxylated and minimally swellable polymers are produced for use as ion exchange matrices, for example, acrylic polymer beads, BioRex 70 resin, 200–400 mesh, BioRad Laboratories, Inc., Hercules, Calif.

Another means of increasing polymer concentration and hence buffering power is to microencapsulate a swellable polymer in a coating that would constrain swelling and entanglement (hence viscosity) yet allow diffusion of protons and counterions.

Furthermore, mixtures of different polycarboxylated polymers could be used to achieve specific advantageous characteristics of buffering power, viscosity, lubricity, and bioadhesion.

Carboxylated polymers other than polyacrylic acids can be used for the present invention, for example, those created by the copolymerization of monounsaturated mono- and dicarboxylated monomers (methacrylic acid, maleic acid, and others) with suitable crosslinking agents known in the art. Moreover, buffering polymers other than carboxylated polymers could be used for this purpose so long as their pKa's are in the appropriate range (i.e., 4.0–7.0), and the polymers are nontoxic and large enough to prevent rapid diffusion through mucosal surfaces.

When a women is desiring to conceive, there is no method now available that will protect her against STDs. Since sperm are less easily killed by brief exposure to acid than many STD pathogens and since sperm are far more motile and can more readily escape contact with the buffering gel, our method also provides a means to achieve significant STD protection while still allowing conception. The method can provide this differential protection (microbicidal but non-contraceptive) by using a buffer capacity comparable, but not greatly exceeding the capacity needed to acidify the ejaculate to pH 5. Contrariwise, the method can be optimized to provide maximum protection against both pregnancy and disease by using higher buffer capacity and also by combining the buffering gel with a cervical barrier, for example, a vaginal diaphragm or cervical cap. Such mechanical barriers will greatly prolong contact of sperm with acid by preventing their rapid entry into the cervical canal.

Finally, the method can also be used to deliver and provide sustained release of one or more beneficial agents to a given area. The agents can be added to the gel and applied to skin or mucosal surfaces such as the ear canal, nasal canal, mouth, vagina or rectum. Thus, the method can be used to deliver agents to skin and biological orifices while, at the same time, maintaining or controlling the pH of these areas. While the method invention has been described in connection with what is presently considered to be the most practical and preferred embodiments, it is to be understood that the method invention is not to be limited to the disclosed embodiments, but on the contrary is intended to cover various modifications and equivalent arrangements included within the spirit and scope of the appended claims. The following patents and scientific articles have been cited throughout this application and the entire contents of each patent and article is hereby incorporated by reference.

U.S. Patents:

U.S. Pat. No. 2,141,040
U.S. Pat. No. 2,616,426
U.S. Pat. No. 3,015,598
U.S. Pat. No. 3,091,241
U.S. Pat. No. 3,128,767
U.S. Pat. No. 3,216,422
U.S. Pat. No. 3,983,874
U.S. Pat. No. 4,274,410
U.S. Pat. No. 4,360,013
U.S. Pat. No. 4,369,773
U.S. Pat. No. 4,393,871
U.S. Pat. No. 4,634,438
U.S. Pat. No. 4,634,439
U.S. Pat. No. 4,848,363

SCIENTIFIC ARTICLES

Holst E, and Brandberg A., Scand. J. Infectious Diseases 22: 625–626, 1990.

Kempf C, Jentsch P, Poirier B, et al., Transfusion 31: 423–427, 1991.

Leveen H H, et al., Annals of Surgery, 178: 745–753, 1973.

Martin L S, McDougal J S, and Loskoski S L, Journal of Infectious Diseases 152: 400–403, 1985.

McCutchan J A, Wunderlich A, and Braude A I, Infection and Immunity 15: 149–155, 1977.

Schlievert P M, and Blomster D A, Journal of Infectious Diseases 147: 236–242, 1983.

What is claimed is:

1. A device for controlling pH by acidic buffering, comprising:
   a) a flexible circular rim and
   b) a flexible, impervious dome having a concave surface, a convex surface and a margin,
   wherein said dome is continuously attached at said margin to said circular rim,
   wherein said device contains between 0.1 and 10 grams of an acidic absorbent buffer and wherein said acidic absorbent buffer has a buffering capacity to maintain a pH less than or equal to 5 after an addition of between 0.014 g to 1.4 g of sodium hydroxide in said device, and wherein said acidic absorbent buffer is comprised of at least one polymer comprised of monomers selected from the group consisting of monounsaturated monocarboxylated monomers and monounsaturated dicarboxylated monomers.

2. The device of claim 1, wherein said buffer is crosslinked polyacrylic acid.

3. The device of claim 1, wherein said dome is covered by a fenestrated coverstock.

4. The device of claim 3, wherein said coverstock is non-adhesive to mucus epithelia.

5. The device of claim 4, wherein said coverstock is selected from the group consisting of non-absorptive and minimally absorptive material.

6. The device of claim 1, wherein said buffer is contained on said concave surface of said dome.

7. The device of claim 1, wherein said buffer is contained on said convex surface of said dome.

8. The device of claim 1, wherein said buffer is contained on said concave surface and said convex surface of said dome.

9. The device of claim 1, wherein at least a portion of said device is reusable.

10. The device of claim 1, wherein the pH is controlled within the range of 3.0 to 5.0.

11. The device of claim 1, wherein said device is also used to deliver at least one additional beneficial agent.

12. A method for controlling pH by acidic buffering, comprising:
   inserting the device of claim 1 into the vaginal cavity of a woman.

13. A method for the inactivation of pathogens, comprising:
   inserting into the vaginal cavity of a woman a device comprised of:
   a) a flexible circular rim and
   b) a flexible dome having a concave surface, a convex surface and a margin,
   wherein said dome is continuously attached at said margin to said circular rim and
   wherein said device contains between 0.1 and 10 grams of an acidic absorbent buffer and wherein said acidic absorbent buffer has a buffering capacity to maintain a pH less than or equal to 5 after an addition of between 0.014 g to 1.4 g of sodium hydroxide in said device.

14. The method of claim 13, wherein said acidic absorbent buffer is comprised of at least one polymer comprised of monomers selected from the group consisting of monounsaturated monocarboxylated monomers and monounsaturated dicarboxylated monomers.

* * * * *